US011607109B2

(12) United States Patent
Usuda

(10) Patent No.: US 11,607,109 B2
(45) Date of Patent: Mar. 21, 2023

(54) ENDOSCOPIC IMAGE PROCESSING DEVICE, ENDOSCOPIC IMAGE PROCESSING METHOD, ENDOSCOPIC IMAGE PROCESSING PROGRAM, AND ENDOSCOPE SYSTEM

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 229 days.

(21) Appl. No.: 16/813,709

(22) Filed: Mar. 9, 2020

(65) Prior Publication Data
US 2020/0294227 A1 Sep. 17, 2020

(30) Foreign Application Priority Data
Mar. 13, 2019 (JP) .............................. JP2019-045786

(51) Int. Cl.
*G06T 7/00* (2017.01)
*A61B 1/00* (2006.01)
(Continued)

(52) U.S. Cl.
CPC ...... *A61B 1/000094* (2022.02); *A61B 1/0005* (2013.01); *A61B 1/00042* (2022.02);
(Continued)

(58) Field of Classification Search
CPC ......... G06T 7/0012; G06T 2207/10068; G06T 2207/30096; A61B 1/0005; A61B 1/045; A61B 1/122
See application file for complete search history.

(56) References Cited

U.S. PATENT DOCUMENTS

2011/0066979 A1* 3/2011 Matsui .................. G06F 3/0236
715/823
2018/0098690 A1 4/2018 Iwaki
(Continued)

FOREIGN PATENT DOCUMENTS

JP H09223155 8/1997
JP 2006191989 7/2006
(Continued)

OTHER PUBLICATIONS

Office Action of Japan Counterpart Application, with English translation thereof, dated Jan. 12, 2021, pp. 1-11.

*Primary Examiner* — Vu Le
*Assistant Examiner* — Winta Gebreslassie
(74) *Attorney, Agent, or Firm* — JCIPRNET

(57) ABSTRACT

There are provided an endoscopic image processing device, an endoscopic image processing method, an endoscopic image processing program, and an endoscope system that appropriately notify region-of-interest information about a region of interest included in an endoscopic image according to an endoscope operator's action.
An endoscope operator's action on a portion to be observed of an endoscopic image is recognized from endoscopic images, and first emphasis display where region-of-interest information is displayed in the endoscopic image at a first emphasis level and second emphasis display where the region-of-interest information is displayed at a second emphasis level relatively lower than the first emphasis level are switched according to a recognition result.

14 Claims, 10 Drawing Sheets

(51) Int. Cl.
  *A61B 1/12*      (2006.01)
  *A61B 1/045*     (2006.01)

(52) U.S. Cl.
  CPC .............. *A61B 1/045* (2013.01); *A61B 1/122* (2013.01); *G06T 7/0012* (2013.01); *G06T 2207/10068* (2013.01); *G06T 2207/30096* (2013.01)

(56) References Cited

U.S. PATENT DOCUMENTS

| | | | |
|---|---|---|---|
| 2018/0114319 A1 | 4/2018 | Kono et al. | |
| 2018/0242817 A1* | 8/2018 | Imaizumi | A61B 1/00055 |
| 2018/0310809 A1* | 11/2018 | Watanabe | A61B 1/00179 |
| 2019/0183322 A1* | 6/2019 | Yamaguchi | G16H 30/40 |
| 2021/0153721 A1* | 5/2021 | Kitamura | A61B 1/00009 |

FOREIGN PATENT DOCUMENTS

| | | |
|---|---|---|
| WO | 2016199273 | 12/2016 |
| WO | 2017002184 | 1/2017 |

* cited by examiner

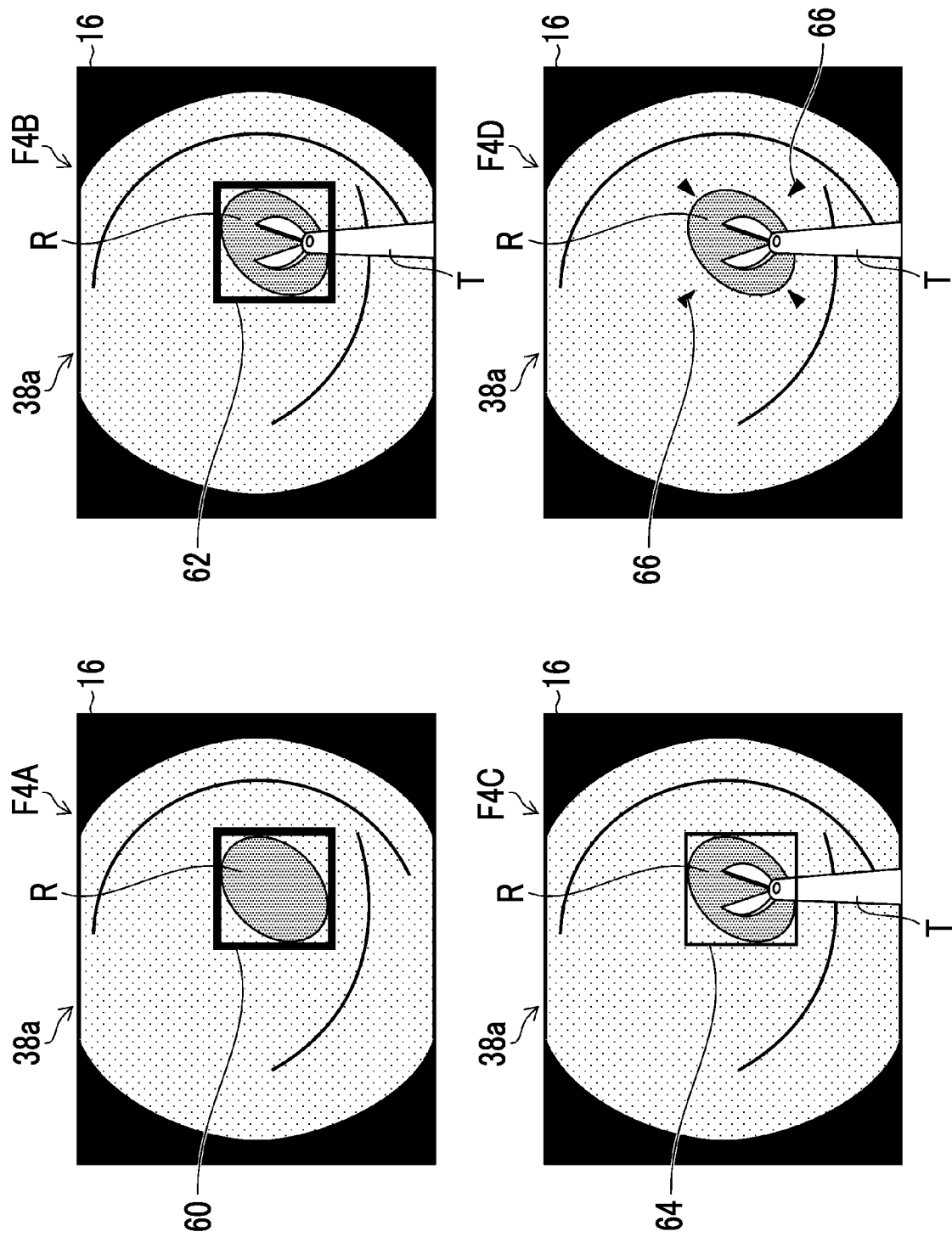

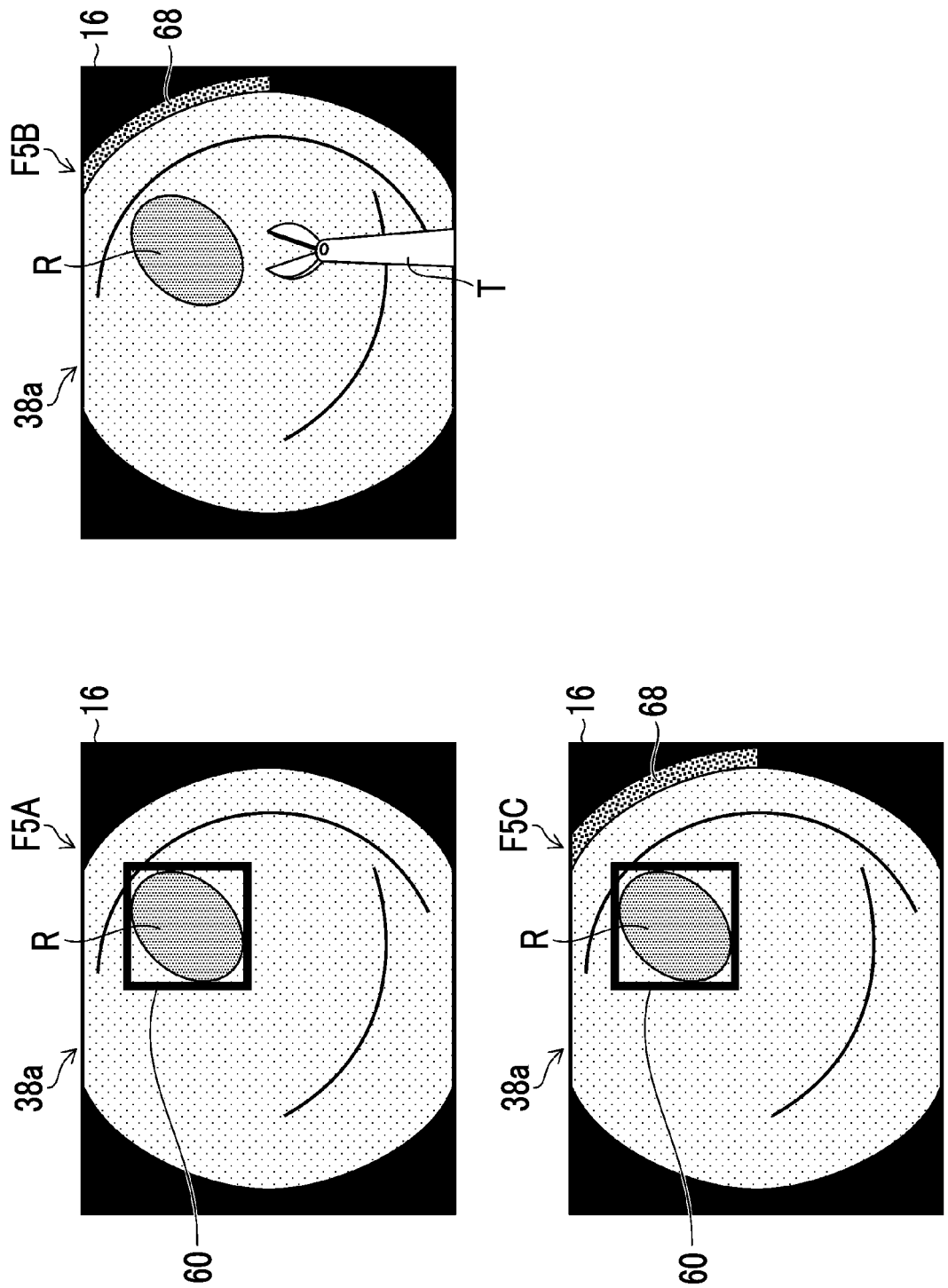

FIG. 6

| ACTION | AUTOMATIC DETECTION CONTROL | EMPHASIS DISPLAY METHOD AT THE TIME OF RECOGNITION OF ACTION | EMPHASIS LEVEL AT THE TIME OF RECOGNITION OF ACTION (0 TO10) | .... |
|---|---|---|---|---|
| USE OF TREATMENT TOOL | ON | FRAME SUPERIMPOSITION (TRANSPARENT) | 5 | |
| WASHING | ON | FRAME SUPERIMPOSITION (LINE THICKNESS) | 3 | |
| ENLARGEMENT OBSERVATION | ON | FOUR-CORNER FIGURE SUPERIMPOSITION | - | |
| PIGMENT OBSERVATION | ON | DISPLAY ONLY OUTSIDE SCREEN | - | |
| INSERTION | OFF | - | - | |
| ⋮ | | | | |

FIG. 7

| ACTION | PRIORITY | AUTOMATIC DETECTION CONTROL | EMPHASIS DISPLAY METHOD AT THE TIME OF RECOGNITION OF ACTION | EMPHASIS LEVEL AT THE TIME OF RECOGNITION OF ACTION (0 TO10) | .... |
|---|---|---|---|---|---|
| USE OF TREATMENT TOOL | 1 | ON | FRAME SUPERIMPOSITION (TRANSPARENT) | 5 | |
| WASHING | 2 | ON | FRAME SUPERIMPOSITION (LINE THICKNESS) | 3 | |
| ENLARGEMENT OBSERVATION | 3 | ON | FOUR-CORNER FIGURE SUPERIMPOSITION | - | |
| PIGMENT OBSERVATION | 4 | ON | DISPLAY ONLY OUTSIDE SCREEN | - | |
| INSERTION | 5 | OFF | - | - | |
| ⋮ | | | | | |

FIG. 8

| ACTION | AUTOMATIC DETECTION CONTROL | EMPHASIS DISPLAY METHOD AT THE TIME OF RECOGNITION OF ACTION | EMPHASIS LEVEL AT THE TIME OF RECOGNITION OF ACTION (0 TO 10) | .... |
|---|---|---|---|---|
| USE OF TREATMENT TOOL | ON | FRAME SUPERIMPOSITION (TRANSPARENT) | 3 | |
| WASHING | OFF | - | - | |
| ENLARGEMENT OBSERVATION | ON | FRAME SUPERIMPOSITION (TRANSPARENT) | 0 | |
| PIGMENT OBSERVATION | ON | FRAME SUPERIMPOSITION (TRANSPARENT) | 0 | |
| INSERTION | ON | FRAME SUPERIMPOSITION (TRANSPARENT) | 0 | |
| ⋮ | | | | |

ENDOSCOPIC IMAGE PROCESSING DEVICE, ENDOSCOPIC IMAGE PROCESSING METHOD, ENDOSCOPIC IMAGE PROCESSING PROGRAM, AND ENDOSCOPE SYSTEM

CROSS-REFERENCE TO RELATED APPLICATIONS

The present application claims priority under 35 U.S.C. § 119 to Japanese Patent Application No. 2019045786, filed on Mar. 13, 2019. The above application is hereby expressly incorporated by reference, in its entirety, into the present application.

BACKGROUND OF THE INVENTION

1. Field of the Invention

The present invention relates to an endoscopic image processing device, an endoscopic image processing method, an endoscopic image processing program, and an endoscope system, and more particularly, to a technique that displays information about a region of interest included in an endoscopic image.

2. Description of the Related Art

An image recognition technique that automatically recognizes a region of interest, such as a lesion, from endoscopic images and notifies a recognition result is known. In a case where the result of recognition of the endoscopic images is notified to a doctor being making an examination using an endoscope, appropriate notification is required according to the step of examination.

For example, a case where a lesion needs to be detected from endoscopic images being observed is limited to a timing when a lesion newly appears in the field of view or a timing when a lesion intermittently disappears from a field of view. On the other hand, since it is certain that a doctor recognizes the presence of a lesion after treatment for a lesion is started by a treatment tool or after detailed observation and diagnosis are started through the application of a pigment, there is a concern that the notification of the position of a lesion may hinder the work of the doctor.

With regard to this problem, WO2017/002184A discloses a technique that determines an operator's action, such as the use of a treatment tool, and determines whether or not an image is an image for the detection of a lesion.

SUMMARY OF THE INVENTION

However, there is an intentional problem in the technique disclosed in WO2017/002184A that the detection of a lesion is not performed during a specific action.

For example, WO2017/002184A discloses that an image is not regarded as an image for detection during a washing action. However, residues are removed during a washing action and an object to be detected may appear on the screen. There is a risk that an object to be detected is missed as long as detection and notification is not made in this case. Accordingly, the results of detection need to continue to be notified regardless of an operator's action.

The invention has been made in consideration of the above-mentioned circumstances, and an object of the invention is to provide an endoscopic image processing device, an endoscopic image processing method, an endoscopic image processing program, and an endoscope system that appropriately notify region-of-interest information about a region of interest included in an endoscopic image according to an endoscope operator's action.

To achieve the object, an endoscopic image processing device according to an aspect comprises a display control unit that causes a display unit to display region-of-interest information about a region of interest included in a plurality of endoscopic images of a portion to be observed sequentially picked up by an endoscope operator and to be sequentially displayed on the display unit, and an action recognition unit that recognizes an endoscope operator's action on the portion to be observed from at least some endoscopic images of the plurality of endoscopic images. The display control unit switches between first emphasis display where the region-of-interest information is displayed at a position in the endoscopic image at a first emphasis level and second emphasis display where the region-of-interest information is displayed at a second emphasis level relatively lower than the first emphasis level, according to a recognition result of the action recognition unit.

According to this aspect, since first emphasis display where the region-of-interest information is displayed at a position in the endoscopic image at a first emphasis level and second emphasis display where the region-of-interest information is displayed at a second emphasis level relatively lower than the first emphasis level are switched according to a recognition result of the action recognition unit, the region-of-interest information about a region of interest included in the endoscopic images can be appropriately notified according to an endoscope operator's action.

It is preferable that the endoscopic image processing device further comprises an image acquisition unit that acquires the plurality of endoscopic images, a region-of-interest detection unit that detects the region of interest from the acquired endoscopic images, and a region-of-interest information acquisition unit that acquires the region-of-interest information about the detected region of interest. Accordingly, the region-of-interest information can be appropriately acquired.

It is preferable that the display control unit causes the display unit to sequentially display the plurality of acquired endoscopic images. Accordingly, the plurality of endoscopic images can be appropriately displayed.

It is preferable that the action recognition unit recognizes whether or not a specific action is performed and the display control unit performs the first emphasis display in a case where the action recognition unit does not recognize the specific action and performs the second emphasis display in a case where the action recognition unit recognizes the specific action. Accordingly, emphasis display can be switched according to the endoscope operator's specific action.

It is preferable that the specific action is at least one action of a use of a treatment tool, washing, enlargement observation, or pigment observation. Accordingly, emphasis display can be switched according to at least one action of the use of a treatment tool, washing, enlargement observation, or pigment observation that is performed by an endoscope operator.

It is preferable that the display control unit displays a figure based on the region-of-interest information. Accordingly, the region-of-interest information can be appropriately notified.

It is preferable that at least one of a color, a shape, or transparency of the figure at the first emphasis level is different from that at the second emphasis level. Accordingly, the emphasis levels can be made to be appropriately different from each other.

It is preferable that the region-of-interest information is displayed at a position different from the endoscopic image in the first emphasis display. Since the region-of-interest information is displayed at a position in the endoscopic image and the region-of-interest information is displayed at a position different from the endoscopic image, the first emphasis level can be made relatively high.

It is preferable that the region-of-interest information is displayed at a position in the endoscopic image in the second emphasis display. Accordingly, the region-of-interest information can be appropriately notified even in the second emphasis level that is relatively low.

It is preferable that the region-of-interest information is displayed at a position different from the endoscopic image in the second emphasis display. Accordingly, the region-of-interest information can be notified without the hindrance of the visual recognition of the endoscopic image.

It is preferable that the endoscopic image processing device further comprises an emphasis method storage section that stores an emphasis method for the region-of-interest information and the display control unit displays the region-of-interest information by the emphasis method stored in the emphasis method storage section. Accordingly, the region-of-interest information can be appropriately notified.

It is preferable that the emphasis method storage section stores the emphasis method for each action recognized by the action recognition unit. Accordingly, the region-of-interest information can be appropriately notified for each action.

It is preferable that the endoscopic image processing device further comprises an input unit that sets the emphasis method and stores the emphasis method in the emphasis method storage section. Accordingly, the second emphasis display according to the endoscope operator can be performed.

To achieve the object, an endoscope system according to another aspect comprises a display unit, an endoscope that is to be inserted into an object to be examined, a camera that sequentially picks up a plurality of endoscopic images of a portion to be observed included in the object to be examined, and the endoscopic image processing device.

According to this aspect, since first emphasis display where the region-of-interest information is displayed at a position in the endoscopic image at a first emphasis level and second emphasis display where the region-of-interest information is displayed at a second emphasis level relatively lower than the first emphasis level are switched according to a recognition result of the action recognition unit, the region-of-interest information about a region of interest included in the endoscopic images can be appropriately notified according to an endoscope operator's action.

To achieve the object, an endoscopic image processing method according to another aspect comprises a display control step of causing a display unit to display region-of-interest information about a region of interest included in a plurality of endoscopic images of a portion to be observed sequentially picked up by an endoscope operator and to be sequentially displayed on the display unit, and an action recognition step of recognizing an endoscope operator's action on the portion to be observed from at least some endoscopic images of the plurality of endoscopic images. First emphasis display where the region-of-interest information is displayed at a position in the endoscopic image at a first emphasis level and second emphasis display where the region-of-interest information is displayed at a second emphasis level relatively lower than the first emphasis level are switched in the display control step according to a recognition result of the action recognition step.

According to this aspect, since first emphasis display where the region-of-interest information is displayed at a position in the endoscopic image at a first emphasis level and second emphasis display where the region-of-interest information is displayed at a second emphasis level relatively lower than the first emphasis level are switched according to a recognition result of the action recognition unit, the region-of-interest information about a region of interest included in the endoscopic images can be appropriately notified according to an endoscope operator's action.

A program causing a computer to perform the endoscopic image processing method is also included in this aspect.

According to the invention, it is possible to appropriately notify region-of-interest information about a region of interest included in an endoscopic image according to an endoscope operator's action.

BRIEF DESCRIPTION OF THE DRAWINGS

FIG. 4 is a diagram showing examples of the display of a display section 16 in a case where a region of interest is detected.

FIG. 5 is a diagram showing examples of the display of the display section 16 in a case where a region of interest is detected.

FIG. 6 is a diagram showing an example of a table that is stored in an emphasis method storage section 50.

FIG. 7 is a diagram showing an example of a table that is stored in the emphasis method storage section 50.

FIG. 8 is a diagram showing an example of a table that is stored in the emphasis method storage section 50.

DESCRIPTION OF THE PREFERRED EMBODIMENTS

Preferred embodiments of the invention will be described in detail below with reference to the accompanying drawings.

Overall Configuration of Endoscope System

Figure 1:
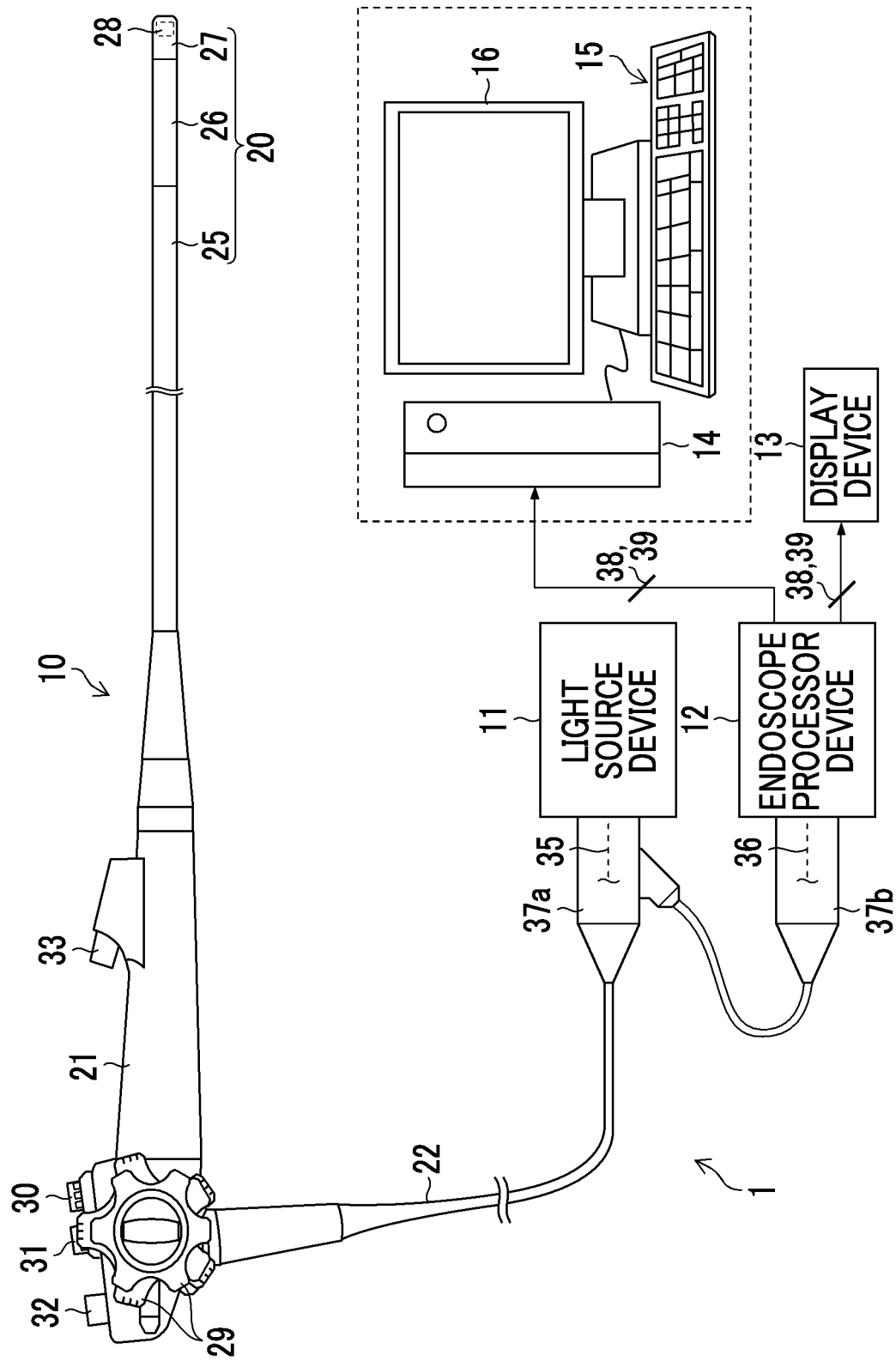
FIG. 1 is a schematic diagram showing the overall configuration of an endoscope system 1 including an endoscopic image processing device according to an embodiment.

FIG. 1 is a schematic diagram showing the overall configuration of an endoscope system 1 including an endoscopic image processing device according to an embodiment. The endoscope system 1 is an apparatus that picks up the endoscopic image of a portion to be observed in the body of an object to be examined (in an object to be examined), automatically recognizes a region of interest, such as a lesion, from the endoscopic image picked up, and notifies the result of the recognition.

As shown in FIG. 1, the endoscope system 1 comprises an endoscope 10 that is an electronic endoscope, a light source device 11, an endoscope processor device 12, a display device 13, an endoscopic image processing device 14, an operation unit 15, and a display section 16.

The endoscope 10 corresponds to a time-series image acquisition unit that acquires time-series images including subject images, and is, for example, a flexible endoscope. The endoscope 10 includes an insertion part 20 that is to be inserted into an object to be examined and includes a distal end and a proximal end, a hand operation part 21 that is connected to the proximal end side of the insertion part 20 and allows an endoscope operator (doctor) to perform various operations in a state in which the endoscope operator grips the hand operation part 21, and a universal cord 22 that is connected to the hand operation part 21.

The entire insertion part 20 is formed in an elongated shape so as to have a small diameter. A soft part 25 having flexibility, a bendable part 26 which is can be bent by the operation of the hand operation part 21, and a distal end part 27 are connected in this order from the proximal end of the insertion part 20 toward the distal end thereof, so that the insertion part 20 is formed.

An image pickup unit 28 that includes an objective lens and an image pickup element (not shown), and the like are built in the distal end part 27. The image pickup element is a complementary metal oxide semiconductor (CMOS) image pickup element or a charge coupled device (CCD) image pickup element. The image light of a portion to be observed is incident on the image pickup surface of the image pickup element through an observation window (not shown) that is opened to the distal end face of the distal end part 27 and the objective lens (not shown) that is disposed in the rear of the observation window. The image pickup element picks up an image using the image light of the portion to be observed that is incident on the image pickup surface thereof (converts the image light into electrical signals), and outputs image pickup signals.

The hand operation part 21 is provided with various operation members that are to be operated by an endoscope operator. Specifically, the hand operation part 21 is provided with two kinds of bending operation knobs 29 that are used for an operation for bending the bendable part 26, an air/water supply button 30 for an operation for supplying air/water, and a suction button 31 for a suction operation. Further, the hand operation part 21 is provided with a static image-pickup-instruction part 32 that is used to give an instruction to pick up a static image 39 of a portion to be observed, and a treatment tool inlet 33 through which a treatment tool (not shown) is inserted into a treatment tool-insertion passage (not shown) inserted into the insertion part 20.

The universal cord 22 is a connection cord that is used to connect the endoscope 10 to the light source device 11. The universal cord 22 includes a light guide 35, a signal cable 36, and a fluid tube (not shown) that are inserted into the insertion part 20 and are provided therein. Further, the end portion of the universal cord 22 is provided with a connector 37a that is to be connected to the light source device 11 and a connector 37b that is branched from the connector 37a and is to be connected to the endoscope processor device 12.

In a case where the connector 37a is connected to the light source device 11, the light guide 35 and the fluid tube (not shown) are inserted into the light source device 11. Accordingly, illumination light, water, and gas to be required are supplied to the endoscope 10 from the light source device 11 through the light guide 35 and the fluid tube (not shown). As a result, the portion to be observed is irradiated with illumination light from an illumination window (not shown) provided on the distal end face of the distal end part 27. Further, gas or water are jetted to an observation window (not shown), which is provided on the distal end face, from an air/water supply nozzle (not shown) provided on the distal end face of the distal end part 27 according to an operation for pressing the above-mentioned air/water supply button 30.

In a case where the connector 37b is connected to the endoscope processor device 12, the signal cable 36 and the endoscope processor device 12 are electrically connected to each other. The image pickup signals of the portion to be observed are output to the endoscope processor device 12 from the image pickup unit 28 of the endoscope 10 through the signal cable 36, and controls signals are output to the endoscope 10 from the endoscope processor device 12.

The light source device 11 supplies illumination light to the light guide 35 of the endoscope 10 through the connector 37a. Light in various wavelength ranges corresponding to the purpose of observation, such as white light (light in a white-light wavelength range or light in a plurality of wavelength ranges), light in one or a plurality of specific wavelength ranges, and a combination thereof, is selected as the illumination light. The specific wavelength range is a wavelength range narrower than a white-light wavelength range.

A first example of the specific wavelength range is, for example, a blue-light wavelength range or a green-light wavelength range of a visible-light wavelength range. The first example of the wavelength range includes a wavelength range of 390 nm to 450 nm or 530 nm to 550 nm, and light of the first example has a peak wavelength in a wavelength range of 390 nm to 450 nm or 530 nm to 550 nm.

A second example of the specific wavelength range is, for example, a red-light wavelength range of a visible-light wavelength range. The second example of the wavelength range includes a wavelength range of 585 nm to 615 nm or 610 nm to 730 nm, and light of the second example has a peak wavelength in a wavelength range of 585 nm to 615 nm or 610 nm to 730 nm.

A third example of the specific wavelength range includes a wavelength range where a light absorption coefficient in oxyhemoglobin is different from that in reduced hemoglobin, and light of the third example has a peak wavelength in a wavelength range where a light absorption coefficient in oxyhemoglobin is different from that in reduced hemoglobin. The third example of the wavelength range includes a wavelength range of 400±10 nm, 440±10 nm, 470±10 nm, or 600 nm to 750 nm, and light of the third example has a peak wavelength in a wavelength range of 400±10 nm, 440±10 nm, 470±10 nm, or 600 nm to 750 nm.

A fourth example of the specific wavelength range is used for the observation of the fluorescence of a fluorescent material present in an object to be examined (fluorescence observation), and is the wavelength range (390 nm to 470 nm) of excitation light that excites the fluorescent material.

A fifth example of the specific wavelength range is an infrared wavelength range. The fifth example of the wavelength range includes a wavelength range of 790 nm to 820 nm or 905 nm to 970 nm, and light of the fifth example has a peak wavelength in a wavelength range of 790 nm to 820 nm or 905 nm to 970 nm.

The endoscope processor device 12 controls the operation of the endoscope 10 through the connector 37b and the signal cable 36. Further, the endoscope processor device 12 generates a video 38, which is time-series images (an example of a plurality of endoscopic images) formed of time-series frame images 38a (see FIG. 2) including subject images, on the basis of the image pickup signals that are acquired from the image pickup unit 28 of the endoscope 10 through the connector 37b and the signal cable 36. The frame rate of the video 38 is, for example, 30 fps (frame per second). That is, the image pickup unit 28 corresponds to a camera that sequentially picks up a plurality of frame images 38a.

Further, in a case where the static image-pickup-instruction part 32 is operated on the hand operation part 21 of the endoscope 10, the endoscope processor device 12 acquires one frame image 38a of the video 38 according to the timing of an image pickup instruction in parallel with the generation of the video 38 and sets this frame image 38a as a static image 39.

The video 38 and the static image 39 are the endoscopic images of the inside of an object to be examined. Furthermore, in a case where the video 38 and the static image 39 are images obtained using light in the above-mentioned specific wavelength range (special light), both the video 38 and the static image 39 are special light images. Then, the endoscope processor device 12 outputs the generated video 38 and the generated static image 39 to the display device 13 and the endoscopic image processing device 14, respectively.

The endoscope processor device 12 may generate (acquire) a special light image, which has information about the above-mentioned specific wavelength range, on the basis of a normal light image that is obtained using the above-mentioned white light. In this case, the endoscope processor device 12 functions as a special light image acquisition unit. Further, the endoscope processor device 12 obtains signals in the specific wavelength range by performing an arithmetic operation based on RGB color information of red, green, and blue or CMY color information of cyan, magenta, and yellow that are included in a normal light image.

Further, the endoscope processor device 12 may generate a feature quantity image, such as a publicly known oxygen saturation image, on the basis of at least one of, for example, a normal light image that is obtained using the above-mentioned white light or a special light image that is obtained using light in the above-mentioned specific wavelength range (special light). In this case, the endoscope processor device 12 functions as a feature-quantity-image generation unit. Both of the static image 39 and the video 38 including the normal light image, the special light image, and the feature quantity image are endoscopic images representing results that are obtained from the image pickup or measurement of a human body for the purpose of diagnosis and examination using images.

The display device 13 is connected to the endoscope processor device 12. The display device 13 displays the video 38 and the static image 39 input from the endoscope processor device 12. An endoscope operator performs an operation for moving the insertion part 20 back and forth and the like while checking the video 38 displayed on the display device 13. Further, in a case where an endoscope operator finds a lesion or the like at a portion to be observed, the endoscope operator operates the static image-pickup-instruction part 32 to pick up the static image of the portion to be observed and makes a diagnosis, a biopsy, and the like.

Configuration of Endoscopic Image Processing Device

The endoscopic image processing device 14 is mainly to notify a region of interest, which is included in the time-series images, to an endoscope operator. For example, a personal computer is used as the endoscopic image processing device 14. Further, a keyboard, a mouse, and the like, which are connected to the personal computer by wire or radio, are used as the operation unit 15, and various monitors, such as an LCD monitor, which can be connected to the personal computer, are used as the display section 16 (an example of a display unit). The endoscopic image processing device 14 functions as a diagnosis support device or a medical service support device together with the operation unit 15 and the display section 16.

Figure 2:
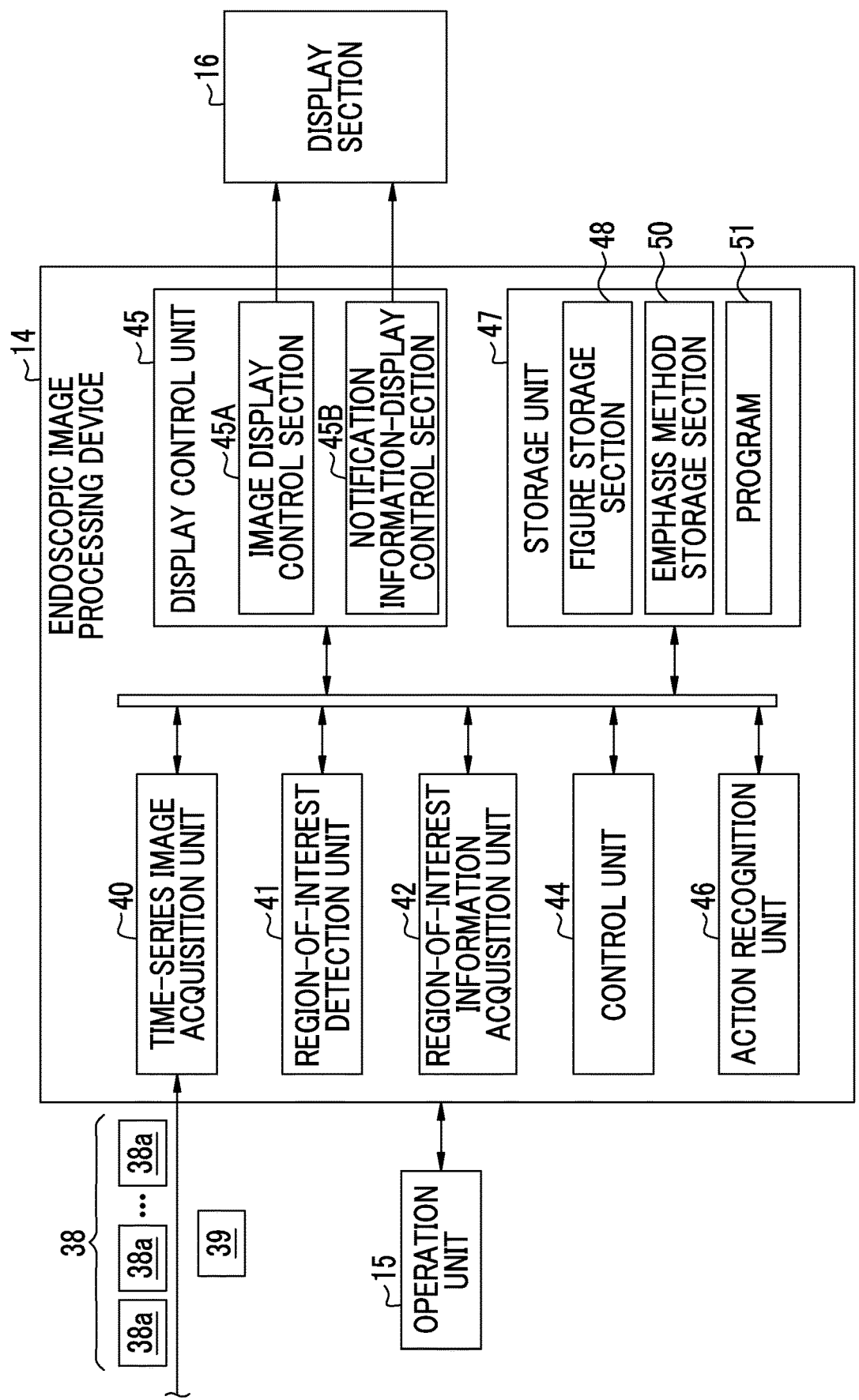
FIG. 2 is a block diagram showing the electrical configuration of the endoscopic image processing device 14.

FIG. 2 is a block diagram showing the electrical configuration of the endoscopic image processing device 14. As shown in FIG. 2, the endoscopic image processing device 14 comprises a time-series image acquisition unit 40, a region-of-interest detection unit 41, a region-of-interest information acquisition unit 42, a control unit 44, a display control unit 45, an action recognition unit 46, and a storage unit 47.

The control unit 44 controls the time-series image acquisition unit 40, the region-of-interest detection unit 41, the region-of-interest information acquisition unit 42, the display control unit 45, and the action recognition unit 46 overall on the basis of a program (endoscopic image processing program) 51 stored in the storage unit 47; and functions as a part of each of these units.

The storage unit 47 stores the static image 39 picked up, the result of detection of the region-of-interest detection unit 41, the program 51, information according to various kinds of control of the endoscopic image processing device 14, and the like. Further, the storage unit 47 comprises a figure storage section 48 that stores figures forming region-of-interest information, which is notification information, and an emphasis method storage section 50 that stores an emphasis method for region-of-interest information.

The time-series image acquisition unit 40 acquires the video 38, which is formed of the time-series frame images 38a including subject images, (the video 38 taken by the endoscope 10 in this embodiment) from the endoscope processor device 12 using an image input/output interface (not shown) that is connected to the endoscope processor device 12 (FIG. 1) by wire or radio. Further, in a case where the above-mentioned static image 39 is picked up while the video 38 is taken by the endoscope 10, the time-series image acquisition unit 40 acquires the video 38 and the static image 39 from the endoscope processor device 12.

The time-series image acquisition unit 40 may acquire the video 38 through various information storage mediums, such as a memory card and a hard disk drive, instead of directly acquiring the video 38 from the endoscope processor device 12. Further, the time-series image acquisition unit 40 may acquire the video 38, which is uploaded to a server, a database, or the like provided on the internet, through the internet.

The region-of-interest detection unit 41 is a unit that detects a region of interest from the video 38 taken during the observation of a portion to be observed. The region-of-interest detection unit 41 calculates the feature quantities of the respective frame images 38a (or frame images 38a thinned out and arranged at a constant interval) of the video 38; includes a convolutional neural network (CNN) for performing processing for recognizing a region of interest present in the images; and calculates feature quantities from color information in the images, the gradient of pixel values, and the like. The region-of-interest detection unit 41 detects a region of interest, such as a lesion in the images, using the calculated feature quantities.

Examples of a region of interest includes a polyp, a cancer, the colonic diverticula, an inflammation, an endoscopic mucosal resection (EMR) scar, an endoscopic submucosal dissection (ESD) scar, a clipped portion, a bleeding point, a perforation, blood vessel heteromorphism, a treatment tool, and the like.

The region-of-interest detection unit 41 can also acquire a recognition result, such as the classification of a category to which a detected region of interest belongs among a plurality of categories about a lesion, such as "tumor", "non-tumor", and "others".

The region-of-interest detection unit 41 is not limited to a case where the region-of-interest detection unit 41 detects a region of interest using a CNN, and may detect a region of interest by analyzing feature quantities, such as colors in images, the gradient of pixel values, a shape, and a size, using image processing.

In a case where a region of interest is detected by the region-of-interest detection unit 41, the region-of-interest information acquisition unit 42 acquires region-of-interest information indicating the region of interest from the region-of-interest detection unit 41. The region-of-interest information is, for example, information about the coordinates of the outline of the region of interest in the images and the feature quantities of the region of interest. The region-of-interest information may be information about whether or not the region of interest is present.

In a case where the time-series image acquisition unit 40 acquires a video 38 with which the region-of-interest information is associated, the region-of-interest information acquisition unit 42 may acquire the region-of-interest information associated with the video 38.

The action recognition unit 46 is a unit that recognizes an endoscope operator's action on the portion to be observed from the video 38 taken during the observation of the portion to be observed. The endoscope operator's action on the portion to be observed includes "use of treatment tool", "washing (water supply)", "enlargement observation", and "pigment observation". The endoscope operator's action on the portion to be observed may include "insertion", "removal", and "length measurement".

The action recognition unit 46 includes a CNN that calculates the feature quantities of the respective frame images 38a of the video 38 to perform processing for recognizing an image, and calculates feature quantities from color information in images, the gradient of pixel values, and the like. The action recognition unit 46 recognizes an endoscope operator's action on the portion to be observed using the calculated feature quantities. The action recognition unit 46 may recognize an endoscope operator's action from at least some frame images 38a of the video 38.

The display control unit 45 comprises an image display control section 45A and a notification information-display control section 45B. The image display control section 45A outputs the video 38, which is acquired by the time-series image acquisition unit 40, to the display section 16 and causes the display section 16 to display the video 38. That is, the plurality of frame images 38a are sequentially displayed on the display section 16.

The notification information-display control section 45B outputs the region-of-interest information, which is acquired by the region-of-interest information acquisition unit 42, to the display section 16. Here, the notification information-display control section 45B outputs the region-of-interest information that is emphasized by the emphasis method stored in the emphasis method storage section 50. Accordingly, the region-of-interest information is displayed on the display section 16 by the emphasis method, which is stored in the emphasis method storage section 50, together with the plurality of frame images 38a.

Further, the notification information-display control section 45B switches between first emphasis display where the region-of-interest information is displayed at a position in the video 38 at a first emphasis level and second emphasis display where the region-of-interest information is displayed at a second emphasis level relatively lower than the first emphasis level, according to the recognition result of the action recognition unit 46. The details of the emphasis display will be described later.

Endoscopic Image Processing Method: First Embodiment

Figure 3:
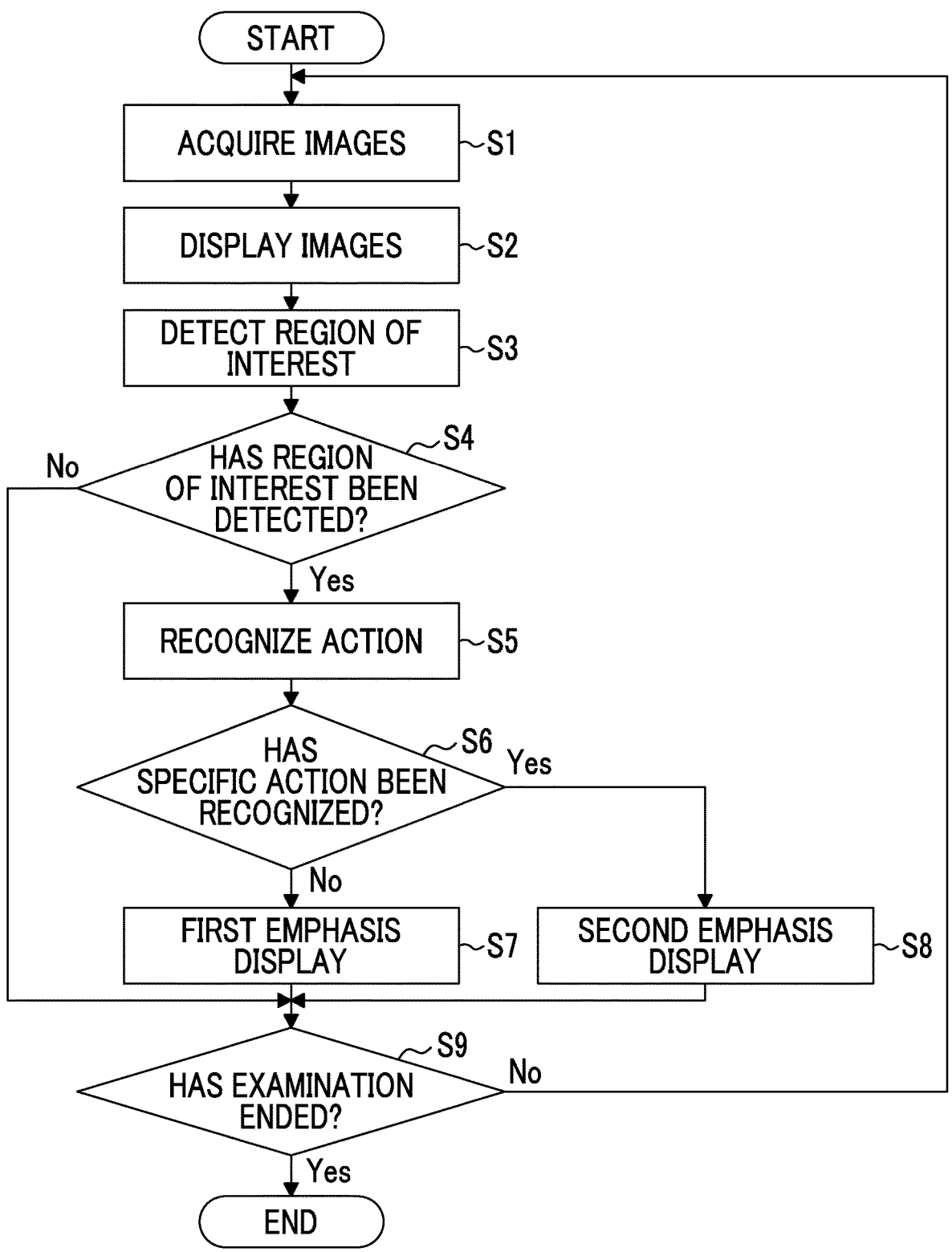
FIG. 3 is a flowchart showing each processing of an endoscopic image processing method according to a first embodiment.

An endoscopic image processing method using the endoscope system 1 will be described. FIG. 3 is a flowchart showing each processing of an endoscopic image processing method according to a first embodiment. The endoscopic image processing method includes an image acquisition step (Step S1), an image display step (Step S2), a region-of-interest detection step (Step S3), an action recognition step (Step S5), a first emphasis display step (Step S7), and a second emphasis display step (Step S8).

In Step S1, the time-series image acquisition unit 40 acquires a plurality of endoscopic images of a portion to be observed that are sequentially picked up by an endoscope operator. Here, the time-series image acquisition unit 40 acquires the frame images 38a of the video 38 that is taken by the endoscope 10.

In Step S2, the image display control section 45A causes the display section 16 to sequentially display the plurality of frame images 38a that are acquired by the time-series image acquisition unit 40. Accordingly, the video 38 is displayed on the display section 16.

In Step S3, the region-of-interest detection unit 41 detects a region of interest from the frame images 38a that are acquired in Step S1. Further, in a case where a region of interest is detected by the region-of-interest detection unit 41, the region-of-interest information acquisition unit 42 acquires region-of-interest information indicating the region of interest from the region-of-interest detection unit 41.

In Step S4, the control unit 44 determines whether or not a region of interest has been detected in Step S3. In a case where a region of interest has been detected, processing proceeds to Step S5. On the other hand, in a case where a region of interest has not been detected, processing proceeds to Step S9.

In Step S5, the action recognition unit 46 recognizes an endoscope operator's action on the portion to be observed from the frame images 38a. In a case where the action recognition unit 46 recognizes that a treatment tool appears in the frame images 38a, the action recognition unit 46 recognizes an endoscope operator's action as "use of treatment tool". In a case where the action recognition unit 46 recognizes that water appears in the frame images 38a, the action recognition unit 46 recognizes an endoscope operator's action as "washing". In a case where the action recognition unit 46 recognizes that the frame images 38a are enlarged and picked up, the action recognition unit 46 recognizes an endoscope operator's action as "enlargement observation". In a case where the action recognition unit 46 recognizes that a pigment appears in the frame images 38a, the action recognition unit 46 recognizes an endoscope operator's action as "pigment observation".

Further, the action recognition unit 46 may determine the moving direction of the insertion part 20 (see FIG. 1) from the plurality of frame images 38a. In a case where the action recognition unit 46 recognizes the moving direction of the insertion part 20 as an insertion direction, the action recognition unit 46 may recognize an endoscope operator's action as "insertion". In a case where the action recognition unit 46 recognizes the moving direction of the insertion part 20 as a removal direction, the action recognition unit 46 may recognize an endoscope operator's action as "removal". Furthermore, the action recognition unit 46 may recognize an endoscope operator's action as "insertion" until the insertion part 20 reaches a turning point in an object to be examined, and may recognize an endoscope operator's action as "removal" after the insertion part 20 reaches the turning point.

Moreover, in a case where the action recognition unit 46 recognizes that a pair of major forceps having gradations or the like appears in the frame images 38*a*, the action recognition unit 46 recognizes an endoscope operator's action as "length measurement". Further, in a case where the action recognition unit 46 recognizes that a marker for the measurement of a length appears in the frame images 38*a*, the action recognition unit 46 recognizes an endoscope operator's action as "length measurement". Light forming a marker is emitted from the distal end of the endoscope by a pointing device, such as a laser and the position of the marker in the image is measured, so that the measurement of a length in this case is performed. Accordingly, in a case where the action recognition unit 46 recognizes a marker for the measurement of a length in the frame images 38*a*, the action recognition unit 46 can recognize an endoscope operator's action as "length measurement".

In Step S6, the control unit 44 determines whether or not a specific action has been recognized in Step S5. Here, the specific action is at least one action of "use of treatment tool", "washing", "enlargement observation", or "pigment observation". In a case where a specific action has not been recognized (in the case of non-recognition), it is determined that a normal observation is made and processing proceeds to Step S7. On the other hand, in a case where a specific action has been recognized, processing proceeds to Step S8.

In Step S7 (an example of a display control step), the notification information-display control section 45B superimposes the region-of-interest information at a position in the video 38 and displays the region-of-interest information at the first emphasis level (first emphasis display).

In Step S8 (an example of the display control step), the notification information-display control section 45B displays the region-of-interest information at the second emphasis level relatively lower than the first emphasis level (second emphasis display).

It is determined in Step S9 whether or not an examination using the endoscope system 1 has ended. The examination ends in a case where an endoscope operator operates the operation unit 15. In a case where the examination has ended, the processing of this flowchart ends. In a case where the examination has not ended, the processing returns to Step S1 and the same processing is repeated.

FIG. 4 is a diagram showing examples of the display of the display section 16 in a case where a region of interest is detected. F4A shown in FIG. 4 denotes a diagram showing an example of the first emphasis display. A region R of interest appears in a frame image 38*a* of F4A. In F4A, a frame-shaped FIG. 60 indicating the position of the detected region R of interest is superimposed and displayed on the frame image 38*a* as region-of-interest information.

Further, F4B shown in FIG. 4 denotes a diagram showing an example of the second emphasis display. A region R of interest and a treatment tool T appear in a frame image 38*a* of F4B. In F4B, an endoscope operator's action is recognized as "use of treatment tool" due to the treatment tool T appearing in the frame image 38*a*. In F4B, a frame-shaped FIG. 62 indicating the position of the detected region R of interest is superimposed and displayed on the frame image 38*a* as region-of-interest information.

The shape, the size, and the line thickness of the FIG. 60 are the same as those of the FIG. 62. Further, the transparency of the FIG. 62 is relatively higher than the transparency of the FIG. 60. Accordingly, the FIG. 60 is the region-of-interest information which is displayed at the first emphasis level, and the FIG. 62 is the region-of-interest information which is displayed at the second emphasis level relatively lower than the first emphasis level.

In the example shown in F4B, the notification information-display control section 45B sets the transparency of the figure of the second emphasis level to transparency higher than the transparency of the figure of the first emphasis level to lower an emphasis level. However, the notification information-display control section 45B may reduce the line thickness of the figure to lower an emphasis level.

F4C shown in FIG. 4 denotes a diagram showing an example of the second emphasis display. A frame image 38*a* of F4C is the same as the frame image 38*a* of F4B. In F4C, a frame-shaped FIG. 64 indicating the position of the detected region R of interest is superimposed and displayed on the frame image 38*a* as region-of-interest information. The shape, the size, and the transparency of the FIG. 60 are the same as those of the FIG. 64. Further, the line thickness of the FIG. 64 is relatively smaller than the line thickness of the FIG. 60. Accordingly, the FIG. 60 emphasizes the region-of-interest information at the first emphasis level, and the FIG. 64 emphasizes the region-of-interest information at the second emphasis level relatively lower than the first emphasis level.

The notification information-display control section 45B may make the figure of the first emphasis level and the figure of the second emphasis level be different from each other to change an emphasis level.

F4D shown in FIG. 4 denotes a diagram showing an example of the second emphasis display. A frame image 38*a* of F4D is the same as the frame image 38*a* of F4B. In F4D, four triangular FIG. 66, which are disposed at the positions of four corners of a rectangle surrounding the detected region R of interest, are superimposed and displayed on the frame image 38*a* as region-of-interest information. The shape of the FIG. 60 is different from that of the FIG. 66. A total area of the four FIG. 66 is relatively smaller than the area of the FIG. 60. Accordingly, the FIG. 60 emphasizes the region-of-interest information at the first emphasis level, and the FIG. 66 emphasizes the region-of-interest information at the second emphasis level relatively lower than the first emphasis level.

The notification information-display control section 45B may change at least two of the shape, the size, and the transparency of the figure to change an emphasis level.

The emphasis methods for the first emphasis display and the second emphasis display are stored in the emphasis method storage section 50 in advance. The notification information-display control section 45B reads the emphasis methods for the first emphasis display and the second emphasis display from the emphasis method storage section 50, and causes the display section 16 to display the region-of-interest information according to the read emphasis methods. Further, the FIG. 60, the FIG. 62, the FIG. 64, and the FIG. 66 are stored in the figure storage section 48.

As described above, the notification information-display control section 45B switches between the first emphasis display where the region-of-interest information is displayed at the first emphasis level and the second emphasis display where the region-of-interest information is displayed at the second emphasis level relatively lower than the first emphasis level, according to the recognition result of the action recognition unit 46. Accordingly, the region-of-interest information about the region of interest included in the frame image 38*a* is appropriately notified according to an endoscope operator's action. That is, in a case where an endoscope operator makes a normal observation, the notification information-display control section 45B superimposes the region-of-interest information at a position in the frame image 38*a* and displays the region-of-interest information at the first emphasis level. Accordingly, since the region-of-interest information is superimposed at a position in the frame image 38*a* in a case where an endoscope operator makes a normal observation, an endoscope operator can easily recognize the region of interest.

Further, in a case where an endoscope operator does not make a normal observation and performs a specific action, the notification information-display control section 45B superimposes the region-of-interest information at a position in the frame image 38*a* and displays the region-of-interest information at the second emphasis level relatively lower than the first emphasis level. Accordingly, even in the case of a specific action, the display of the region-of-interest information does not obstruct an action and the region of interest continues to be detected. Therefore, it is possible to prevent the region of interest from being missed.

Second Embodiment

The emphasis methods for the first emphasis display and the second emphasis display stored in the emphasis method storage section 50 are not limited to the examples shown in FIG. 4. Region-of-interest information may be displayed at a position different from the frame image 38*a* without being superimposed and displayed at a position in the frame image 38*a*.

FIG. 5 is a diagram showing examples of the display of the display section 16 in a case where a region of interest is detected. F5A shown in FIG. 5 denotes a diagram showing an example of the first emphasis display. A region R of interest appears in a frame image 38*a* of F5A. In F5A, a frame-shaped FIG. 60 indicating the position of the detected region R of interest is superimposed and displayed on the frame image 38*a* as region-of-interest information.

Further, F5B shown in FIG. 5 denotes a diagram showing an example of the second emphasis display. A region R of interest and a treatment tool T appear in a frame image 38*a* of F5B. In F5B, an endoscope operator's action is recognized as "use of treatment tool" due to the treatment tool T appearing in the frame image 38*a*. In F5B, an image frame-shaped FIG. 68 indicating the position of the detected region R of interest is displayed at a position in the first quadrant around the frame image 38*a* (an example of a position different from the frame image 38*a*) as region-of-interest information. The FIG. 68 is disposed around any one position of positions corresponding to the first quadrant, the second quadrant, the third quadrant, and the fourth quadrant of the frame image 38*a* according to the position of the detected region R of interest.

Since the FIG. 60 is superimposed at a position in the frame image 38*a*, the emphasis level of the FIG. 60 is relatively high. Further, since the FIG. 68 is displayed at a position different from the frame image 38*a*, the emphasis level of the FIG. 68 is relatively low. Accordingly, the FIG. 60 emphasizes the region-of-interest information at the first emphasis level, and the FIG. 68 emphasizes the region-of-interest information at the second emphasis level relatively lower than the first emphasis level. Therefore, the region-of-interest information about the region of interest included in the frame image 38*a* can be appropriately notified according to an endoscope operator's action.

The image frame-shaped FIG. 68 may be used for the first emphasis display. F5C shown in FIG. 5 denotes a diagram showing an example of the first emphasis display. In F5C, a frame-shaped FIG. 60 indicating the position of a detected region R of interest is superimposed and displayed on a frame image 38*a* and a FIG. 68 is displayed around the frame images 38*a* as region-of-interest information. That is, the region-of-interest information is displayed on both the inside and outside of the frame image 38*a* in the first emphasis display. The region-of-interest information about the region of interest included in the frame image 38*a* can be appropriately notified according to an endoscope operator's action by the switching of the first emphasis display shown in F5C and the second emphasis display shown in FSB.

Third Embodiment

The emphasis method storage section 50 may store an emphasis method for the second emphasis display for each specific action, which is recognized by the action recognition unit 46, as a table. FIG. 6 is a diagram showing an example of a table that is stored in the emphasis method storage section 50.

As shown in FIG. 6, the emphasis method storage section 50 stores "whether automatic detection control is ON or OFF", "emphasis display method at the time of recognition of action", and "emphasis level at the time of recognition of action" for each specific action recognized by the action recognition unit 46, as a table. That is, the emphasis methods mentioned here mean total information about "whether automatic detection control is ON or OFF", "emphasis display method at the time of recognition of action", and "emphasis level at the time of recognition of action".

"Whether automatic detection control is ON or OFF" means whether or not the first emphasis display and the second emphasis display are switched. In a case where automatic detection control is "ON", display is switched on the basis of information, such as "emphasis display method at the time of recognition of action" at the time of recognition of a corresponding action. In a case where automatic detection control is "OFF", an emphasis method for the first emphasis display is continued even though a corresponding action is recognized.

"Emphasis display method at the time of recognition of action" means a figure displayed in the second emphasis display, and is set in a case where "automatic detection control" is "ON". "Frame superimposition (transparent)" is a method of changing the transparency of a figure from the first emphasis display as in F4B of FIG. 4. "Frame superimposition (line thickness)" is a method of changing a line thickness from the first emphasis display as in F4C of FIG. 4. "Four-corner figure superimposition" is a method of changing the shape of a figure from the first emphasis display as in F4D of FIG. 4, and is a method of changing a figure to figures that are disposed at the positions of four corners. "Display only outside screen" is a method of changing the disposition of a figure to the disposition of a figure disposed only at a position different from the frame image 38*a* from the first emphasis display as in F5B of FIG. 5.

"Emphasis level at the time of recognition of action" means the second emphasis level, and is set in a case where "emphasis display method at the time of recognition of action" is a specific display method. "Emphasis level at the time of recognition of action" is digitized as a value in the range of 0 to 10. A case where "emphasis level at the time of recognition of action" is the minimum value of "0" is the same as a case where region-of-interest information is not displayed at all. A case where "emphasis level at the time of recognition of action" is the maximum value of "10" is the same as a case where "automatic detection control" is OFF. That is, the value of the first emphasis level is "10".

An example where "emphasis level at the time of recognition of action" is digitized as the stages of 1 to 10 has been described here, but "emphasis level at the time of recognition of action" has only to be digitized as a value indicating an emphasis level.

The notification information-display control section 45B reads an emphasis method for the second emphasis display from the table of the emphasis method storage section 50 according to the recognition result of the action recognition unit 46, and displays the region-of-interest information by the read emphasis method. For example, since automatic detection control is "ON" in a case where the action recognition unit 46 recognizes "use of treatment tool", the notification information-display control section 45B switches emphasis display into the second emphasis display of "frame superimposition (transparent)" of which the second emphasis level is "5". In a case where transparency at an emphasis level of "0" is set to 100% and transparency at an emphasis level of "10" is set to 0%, transparency at an emphasis level of "5" is 50%.

Since automatic detection control is "ON" in a case where the action recognition unit 46 recognizes "washing", the notification information-display control section 45B switches emphasis display into the second emphasis display of "frame superimposition (line thickness)" of which the second emphasis level is "3". In a case where a line thickness at an emphasis level of "0" is set to zero pixel and a line thickness at an emphasis level of "10" is set to 10 pixels, a line thickness at an emphasis level of "3" is 3 pixels.

Since automatic detection control is "ON" in a case where the action recognition unit 46 recognizes "enlargement observation", the notification information-display control section 45B switches emphasis display into the second emphasis display of "four-corner figure superimposition". Since automatic detection control is "ON" in a case where the action recognition unit 46 recognizes "pigment observation", the notification information-display control section 45B switches emphasis display into the second emphasis display of "display only outside screen". "Enlargement observation" and "pigment observation" are examples where an emphasis level cannot be set.

Since automatic detection control is "OFF" in a case where the action recognition unit 46 recognizes "insertion", the notification information-display control section 45B maintain the first emphasis display without switching emphasis display into the second emphasis display. The action recognition unit 46 may stop recognizing an action in a case where automatic detection control is "OFF".

Fourth Embodiment

Priority may be given to the recognition result of the action recognition unit 46 with regard to switching emphasis display into the second emphasis display. FIG. 7 is a diagram showing an example of a table that is stored in the emphasis method storage section 50. In the table shown in FIG. 7, priority is given to each action in addition to the table shown in FIG. 6. Here, higher priority is given to "use of treatment tool", "washing", "enlargement observation", "pigment observation", and "insertion" in this order.

In this embodiment, the notification information-display control section 45B displays region-of-interest information by an emphasis method of an action to which relatively higher priority is given in a case where the action recognition unit 46 simultaneously recognizes a plurality of actions. For example, in a case where the action recognition unit 46 recognizes "use of treatment tool" and "pigment observation", the notification information-display control section 45B employs an emphasis method corresponding to "use of treatment tool" to which relatively higher priority is given. That is, the notification information-display control section 45B switches emphasis display into the second emphasis display of "frame superimposition (transparent)" of which the second emphasis level is "5".

Since priority is given as described above, appropriate emphasis display can be performed in a case where a plurality of actions are recognized.

Further, priority may be automatically set according to the set emphasis method. A criterion used to automatically set priority is, for example, to give high priority to an action of which the emphasis level at the time of recognition of an action is relatively high.

FIG. 8 is a diagram showing an example of a table that is stored in the emphasis method storage section 50. In a case where an action is "use of treatment tool" in this example, as shown in FIG. 8, automatic detection control is "ON", "emphasis display method at the time of recognition of action" is "frame superimposition (transparent)", and "emphasis level at the time of recognition of action" is "3". Further, in a case where an action is "washing", automatic detection control is "OFF". Furthermore, in a case where an action is "pigment observation", automatic detection control is "ON", "emphasis display method at the time of recognition of action" is "frame superimposition (transparent)", and "emphasis level at the time of recognition of action" is "0".

Accordingly, since automatic detection control is "ON" in a case where the action recognition unit 46 recognizes "pigment observation", the notification information-display control section 45B switches emphasis display into the second emphasis display of "frame superimposition (transparent)" of which the second emphasis level is "0" (that is, a frame is not displayed). After that, in a case where the action recognition unit 46 recognizes "use of treatment tool" and "pigment observation", the notification information-display control section 45B give priority to "use of treatment tool" to which relatively higher "emphasis level at the time of recognition of action" is given and switches emphasis display into the second emphasis display of "frame superimposition (transparent)" of which the second emphasis level is "3".

Further, in a case where the action recognition unit 46 recognizes "washing" and "pigment observation" after the action recognition unit 46 recognizes "pigment observation" and emphasis display is switched into the second emphasis display, the notification information-display control section 45B determines that "emphasis level at the time of recognition of action" of "washing" where automatic detection control is "OFF" is relatively higher than that of "pigment observation" and switches emphasis display into the first emphasis display.

Even though where priority is automatically set as described above, appropriate emphasis display can be performed in a case where a plurality of actions are recognized.

Fifth Embodiment

It is preferable that an endoscope operator or the like can change the contents of the table stored in the emphasis method storage section 50 according to one's preference. An example where the display section 16 is caused to display the contents of the current table and an endoscope operator changes the contents of the current table using the operation unit 15 (an example of an input unit) will be described here. In the following description, there is a case where an endoscope operator's operation for using the operation unit 15 to dispose a cursor C (see FIG. 9) on a screen at a desired position and performing a selection action is simply referred to as "the operation of the operation unit 15".

Figure 9:
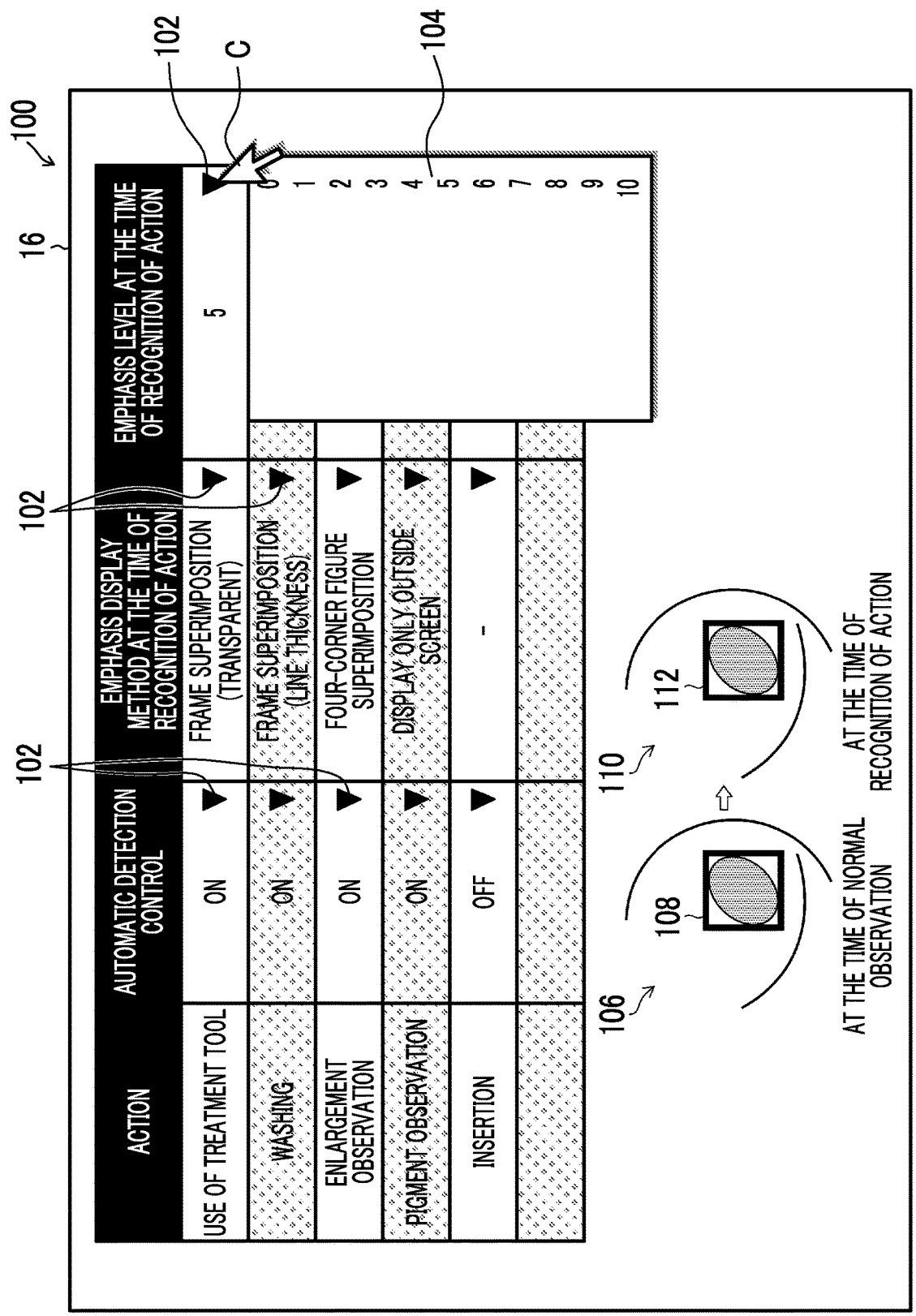
FIG. 9 is a diagram showing a table change screen 100 that is displayed on the display section 16.

FIG. 9 is a diagram showing a table change screen 100 that is an example of a user interface used to change the contents of the table by an endoscope operator or the like and is displayed on the display section 16. The control unit 44 reads a table from the emphasis method storage section 50, and the display control unit 45 causes the display section 16 to display the table change screen 100 on the basis of the read table.

As shown in FIG. 9, the current setting states of "whether automatic detection control is ON or OFF", "emphasis display method at the time of recognition of action", and "emphasis level at the time of recognition of action" for each action are displayed on the table change screen 100. Drop-down buttons 102 are disposed on the right sides of the current setting states, respectively.

In a case where an endoscope operator operates the operation unit 15 to dispose a cursor C at the position of a desired drop-down button 102 and performs a selection action, a pull-down menu 104 is displayed on the table change screen 100. In the example shown in FIG. 9, a drop-down button 102, which is positioned on the right side of the current setting state "5" of "emphasis level at the time of recognition of action" of the action of "use of treatment tool", is selected and a pull-down menu 104 of "emphasis level at the time of recognition of action" is displayed. Here, a value in the range of "0" to "10", which can be set as "emphasis level at the time of recognition of action", is displayed in this pull-down menu 104 so as to be selectable.

In a case where an endoscope operator selects a desired value by the operation of the operation unit 15 from this state, "emphasis level at the time of recognition of action" is changed to the selected value.

Further, the table change screen 100 illustrates how the display of an item, which is being edited by an endoscope operator, will be changed at the time of recognition of an action. A first emphasis display preview 106 and a second emphasis display preview 110 are displayed on the table change screen 100.

A frame-shaped FIG. 108, which is the region-of-interest information of the first emphasis display, is displayed in the first emphasis display preview 106.

Further, since the drop-down button 102 of "emphasis level at the time of recognition of action" of the action of "use of treatment tool" is operated in the example shown in FIG. 9 by the cursor C, the preview of the second emphasis display of the action of "use of treatment tool" is displayed as the second emphasis display preview 110. A frame-shaped FIG. 112, which is the region-of-interest information of the second emphasis display at the time of recognition of the action of "use of treatment tool", is displayed in the second emphasis display preview 110. Here, a FIG. 112 where "emphasis display method at the time of recognition of action" in the current setting state is "frame superimposition (transparent)" and "emphasis level at the time of recognition of action" is "5" is displayed.

Since an endoscope operator visually recognizes the first emphasis display preview 106 and the second emphasis display preview 110, the endoscope operator can check a change in emphasis display.

Finally, in a case where an endoscope operator performs an operation for ending a change in the contents of the table by the operation unit 15, the control unit 44 causes the changed setting states of the table to be stored in the emphasis method storage section 50 and ends processing for changing settings.

The user interface, which is used to change the contents of the table by an endoscope operator or the like, is not limited to the table change screen 100 shown in FIG. 9. For example, the user interface may be a screen that has a hierarchical structure for each action.

Figure 10:
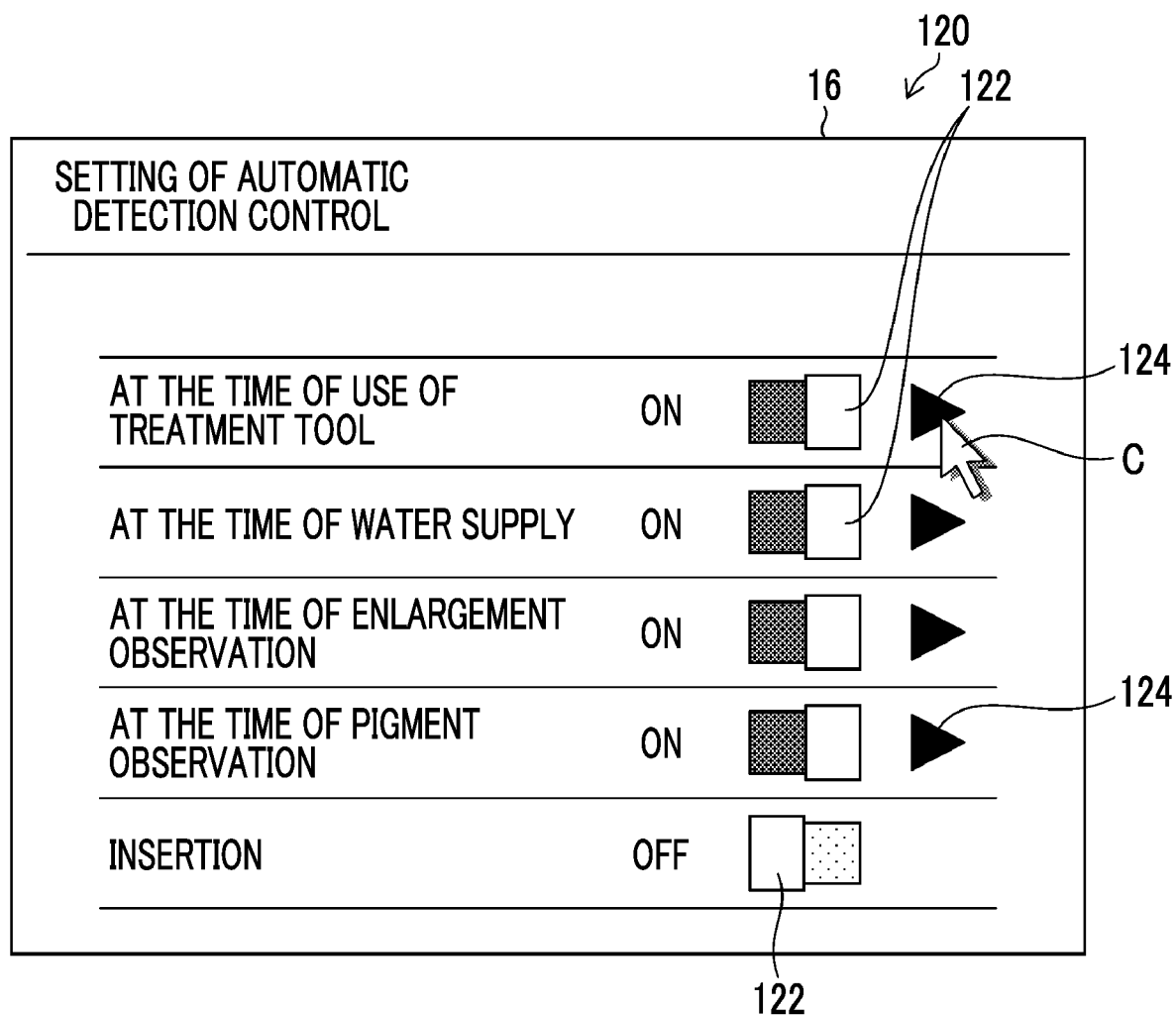
FIG. 10 is a diagram showing a first table change screen 120 that is displayed on the display section 16.
Figure 11:
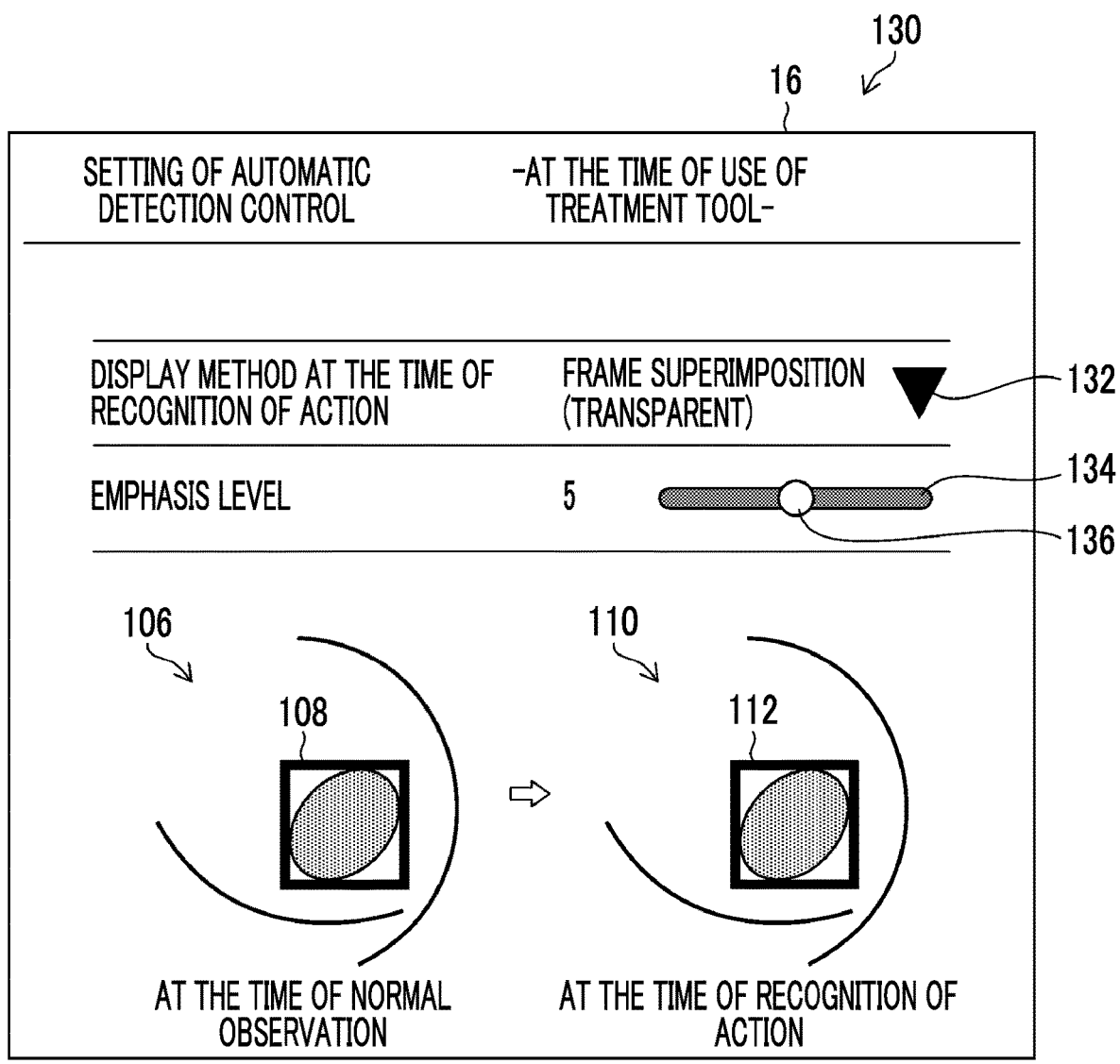
FIG. 11 is a diagram showing a second table change screen 130 that is displayed on the display section 16.

FIGS. 10 and 11 are diagrams showing other examples of a user interface that is used to change the contents of the table by an endoscope operator or the like, and are diagrams showing a first table change screen 120 and a second table change screen 130 that are displayed on the display section 16, respectively. The control unit 44 reads a table from the emphasis method storage section 50, and the display control unit 45 causes the display section 16 to display any one of the first table change screen 120 or the second table change screen 130 on the basis of the read table. The display control unit 45 causes the display section 16 to display the first table change screen 120 first.

The first table change screen 120 is a screen that is used to set whether to make the automatic detection control for the respective actions be ON or OFF. As shown in FIG. 10, ON/OFF buttons 122 used to set whether to make "automatic detection control" be ON or OFF for the respective actions of "use of treatment tool", "washing", "enlargement observation", "pigment observation", and "insertion" are disposed on the first table change screen 120. An endoscope operator can set the ON/OFF button 122 for each action to an ON state or an OFF state by the operation of the operation unit 15. In a case where the ON/OFF button 122 is set to an ON state, "automatic detection control" is ON. In a case where the ON/OFF button 122 is set to an OFF state, "automatic detection control" is OFF.

A shift button 124 is displayed on the right side of the ON/OFF button 122 with regard to an action for which the ON/OFF button 122 is set to an ON state. Since "use of treatment tool", "washing", "enlargement observation", and "pigment observation" are set to an ON state in the example shown in FIG. 10, shift buttons 124 are displayed on the right sides of the ON/OFF buttons 122 therefor. Further, since "insertion" is set to an OFF state, a shift button 124 is not displayed.

In a case where an endoscope operator selects the shift button 124 for any action by the operation of the operation unit 15, the display control unit 45 causes the display section 16 to display the second table change screen 130 on the basis of the read table. FIG. 11 shows a second table change screen 130 corresponding to the action of "use of treatment tool".

The second table change screen 130 is a screen that is used to set "emphasis display method at the time of recognition of action" and "emphasis level at the time of recognition of action" for an action corresponding to the selected shift button 124. The current setting states of "emphasis display method at the time of recognition of action" and "emphasis level at the time of recognition of action" are displayed on the second table change screen 130. Here, "frame superimposition (transparent)" is displayed as "emphasis display method at the time of recognition of action", and "5" is displayed as "emphasis level at the time of recognition of action".

A drop-down button 132 is disposed on the right side of the current setting state of "emphasis display method at the time of recognition of action". In a case where an endoscope operator selects the drop-down button 132 by the operation of the operation unit 15, a pull-down menu (not shown) is displayed. In a case where an endoscope operator selects a desired method from the pull-down menu by the operation of the operation unit 15, "emphasis display method at the time of recognition of action" is changed to the selected method.

Further, a slide bar 134 and a slide button 136 are disposed on the right side of the current setting state of "emphasis level at the time of recognition of action". The slide bar 134 is a figure having the shape of a bar extending in a horizontal direction. Each position in the slide bar 134 corresponds to an emphasis level between an emphasis level of "10" of the leftmost end of the slide bar 134 and an emphasis level of "0" of the rightmost end of the slide bar 134. The slide button 136 is a figure that is disposed to be movable in the slide bar 134. The position of the slide button 136 in the slide bar 134 represents a set emphasis level. In a case where an endoscope operator changes the position of the slide button 136 in the slide bar 134 by the operation of the operation unit 15, "emphasis level at the time of recognition of action" is changed to an emphasis level corresponding to the changed position of the slide button 136.

In a case where "emphasis display method at the time of recognition of action" where "emphasis level at the time of recognition of action" cannot be set like "enlargement observation" and "pigment observation" of third embodiment is selected, the display control unit 45 displays the slide bar 134 and the slide button 136 in an inactive state or does not display the slide bar 134 and the slide button 136.

Further, a first emphasis display preview 106 and a second emphasis display preview 110 are displayed on the second table change screen 130 as in the case of the table change screen 100. The preview of the second emphasis display of "emphasis display method at the time of recognition of action" and "emphasis level at the time of recognition of action" set on the second table change screen 130 is displayed in the second emphasis display preview 110.

In a state where the second table change screen 130 is displayed on the display section 16, an endoscope operator can return a state to a state where the first table change screen 120 is displayed on the display section 16 by the operation unit 15.

In a case where an endoscope operator performs an operation for ending a change in the contents of the table by the operation of the operation unit 15 in a state where the first table change screen 120 is displayed on the display section 16, the control unit 44 causes the emphasis method storage section 50 to store the changed setting state of the table and ends processing for changing settings.

Since the contents of the table stored in the emphasis method storage section 50 are adapted to be changeable as described above, an endoscope operator can set emphasis display according to one's preference.

An example where an endoscope operator sets the contents of the table by using the cursor C has been described here, but an endoscope operator may input characters and the like from a keyboard. Further, the invention is not limited to a case where a table is changed in the endoscopic image processing device 14, and a table may be changed in other personal computers and the like.

Others

The endoscopic image processing method can be formed as a program for causing a computer to perform the respective steps, and a non-temporary recording medium, such as a compact disk-read only memory (CD-ROM), storing this program can also be formed.

In the embodiments described above, for example, the hardware structures of processing units, which perform various kinds of processing of the endoscopic image processing device 14, are various processors to be described below. Various processors include: a central processing unit (CPU) that is a general-purpose processor functioning as various processing units by executing software (program); a graphics processing unit (GPU) that is a processor specialized for image processing; a programmable logic device (PLD) that is a processor of which the circuit configuration can be changed after manufacture, such as a field programmable gate array (FPGA); a dedicated electrical circuit that is a processor having circuit configuration designed exclusively to perform specific processing, such as an application specific integrated circuit (ASIC); and the like.

One processing unit may be formed of one of these various processors, or may be formed of a combination of two or more same kind or different kinds of processors (for example, a plurality of FPGAs, a combination of a CPU and an FPGA, or a combination of a CPU and a GPU). Further, a plurality of processing units may be formed of one processor. As an example where a plurality of processing units are formed of one processor, first, there is an aspect where one processor is formed of a combination of one or more CPUs and software as typified by computers, such as a server and a client, and functions as a plurality of processing units. Second, there is an aspect where a processor fulfilling the functions of the entire system, which includes a plurality of processing units, by one integrated circuit (IC) chip as typified by System On Chip (SoC) or the like is used. In this way, various processing units are formed using one or more of various processors as hardware structures.

Furthermore, the hardware structures of these various processors are more specifically electrical circuitry where circuit elements, such as semiconductor elements, are combined.

The technical scope of the invention is not limited to the scopes described in the above-mentioned embodiments. The components and the like of the respective embodiments can be appropriately combined with each other without departing from the scope of the invention.

EXPLANATION OF REFERENCES

1: endoscope system
10: endoscope
11: light source device
12: endoscope processor device
13: display device
14: endoscopic image processing device
15: operation unit
16: display section
20: insertion part
21: hand operation part
22: universal cord
25: soft part
26: bendable part
27: distal end part
28: image pickup unit 29: bending operation knob
30: air/water supply button
31: suction button
32: static image-pickup-instruction part
33: treatment tool inlet
35: light guide
36: signal cable
37a: connector
37b: connector
38: video
38a: frame image
39: static image
40: time-series image acquisition unit
41: region-of-interest detection unit
42: region-of-interest information acquisition unit
44: control unit
45: display control unit
45A: image display control section
45B: notification information-display control section
46: action recognition unit
47: storage unit
48: figure storage section
50: emphasis method storage section
51: program (endoscopic image processing program)
60: figure
62: figure
64: figure
66: figure
68: figure
100: table change screen
102: drop-down button
104: pull-down menu
106: first emphasis display preview
108: figure
110: second emphasis display preview
112: figure
120: first table change screen
122: ON/OFF button
124: shift button
130: second table change screen
132: drop-down button
134: slide bar
136: slide button

What is claimed is:

1. An endoscopic image processing device comprising:
a processor configured to:
cause a display to display region-of-interest information about a region of interest included in a plurality of endoscopic images of a portion to be observed sequentially picked up by an endoscope operator and to be sequentially displayed on the display;
recognize an endoscope operator's action on the portion to be observed from at least some endoscopic images of the plurality of endoscopic images, and recognize whether or not a specific action is performed, wherein the specific action is at least one action of a use of a treatment tool, washing, length measurement, or pigment observation;
switch between first emphasis display where the region-of-interest information is displayed at a position in the endoscopic image at a first emphasis level and second emphasis display where the region-of-interest information is displayed at a second emphasis level relatively lower than the first emphasis level, according to a recognition result of the processor; and
perform the first emphasis display in a case where the specific action is not recognized, and perform the second emphasis display in a case where the specific action is recognized.

2. The endoscopic image processing device according to claim 1,
wherein the processor is further configured to:
acquire the plurality of endoscopic images;
detect the region of interest from the acquired endoscopic images; and
acquire the region-of-interest information about the detected region of interest.

3. The endoscopic image processing device according to claim 2,
wherein the processor causes the display to sequentially display the plurality of acquired endoscopic images.

4. The endoscopic image processing device according to claim 1,
wherein the processor displays a figure based on the region-of-interest information.

5. The endoscopic image processing device according to claim 4,
wherein at least one of a color, a shape, or transparency of the figure at the first emphasis level is different from that at the second emphasis level.

6. The endoscopic image processing device according to claim 1,
wherein the region-of-interest information is displayed at a position different from the endoscopic image in the first emphasis display.

7. The endoscopic image processing device according to claim 1,
wherein the region-of-interest information is displayed at a position in the endoscopic image in the second emphasis display.

8. The endoscopic image processing device according to claim 1,
wherein the region-of-interest information is displayed at a position different from the endoscopic image in the second emphasis display.

9. The endoscopic image processing device according to claim 1, further comprising:
an emphasis method storage section that stores an emphasis method for the region-of-interest information,
wherein the processor displays the region-of-interest information by the emphasis method stored in the emphasis method storage section.

10. The endoscopic image processing device according to claim 9,
wherein the emphasis method storage section stores the emphasis method for each action recognized by the processor.

11. The endoscopic image processing device according to claim 9, further comprising:
an input unit that sets the emphasis method and stores the emphasis method in the emphasis method storage section, wherein the input unit comprises a keyboard.

12. An endoscope system comprising:
a display;
an endoscope that is to be inserted into an object to be examined;
a camera that sequentially picks up a plurality of endoscopic images of a portion to be observed included in the object to be examined; and
the endoscopic image processing device according to claim 1.

13. An endoscopic image processing method comprising:
- a display control step of causing a display to display region-of-interest information about a region of interest included in a plurality of endoscopic images of a portion to be observed sequentially picked up by an endoscope operator and to be sequentially displayed on the display; and
- an action recognition step of recognizing an endoscope operator's action on the portion to be observed from at least some endoscopic images of the plurality of endoscopic images, and recognizing whether or not a specific action is performed, wherein the specific action is at least one action of a use of a treatment tool, washing, length measurement, or pigment observation,
- wherein first emphasis display where the region-of-interest information is displayed at a position in the endoscopic image at a first emphasis level and second emphasis display where the region-of-interest information is displayed at a second emphasis level relatively lower than the first emphasis level are switched in the display control step according to a recognition result of the action recognition step,
- wherein the display control step further comprises performing the first emphasis display in a case where the specific action is not recognized in the action recognition step, and performing the second emphasis display in a case where the specific action is recognized in the action recognition step.

14. A non-transitory, tangible recording medium which records a program that, when executed by a computer, causes the computer to perform an endoscopic image processing method comprising:
- a display control step of causing a display to display region-of-interest information about a region of interest included in a plurality of endoscopic images of a portion to be observed sequentially picked up by an endoscope operator and to be sequentially displayed on the display; and
- an action recognition step of recognizing an endoscope operator's action on the portion to be observed from at least some endoscopic images of the plurality of endoscopic images, and recognizing whether or not a specific action is performed, wherein the specific action is at least one action of a use of a treatment tool, washing, length measurement, or pigment observation,
- wherein first emphasis display where the region-of-interest information is displayed at a position in the endoscopic image at a first emphasis level and second emphasis display where the region-of-interest information is displayed at a second emphasis level relatively lower than the first emphasis level are switched in the display control step according to a recognition result of the action recognition step,
- wherein the display control step further comprises performing the first emphasis display in a case where the specific action is not recognized in the action recognition step, and performing the second emphasis display in a case where the specific action is recognized in the action recognition step.

* * * * *